United States Patent [19]

Swenson

[11] 4,213,451
[45] * Jul. 22, 1980

[54] TONGUE BLADE FOR MOUTH GAG FOR ADULTS

[76] Inventor: Rudolph E. Swenson, 2748 Ptarmigan Dr. #5, Walnut Creek, Calif. 94595

[*] Notice: The portion of the term of this patent subsequent to Dec. 27, 1994, has been disclaimed.

[21] Appl. No.: 935,514

[22] Filed: Aug. 21, 1978

[51] Int. Cl.² ............................................... A61B 1/00
[52] U.S. Cl. .................................................... 128/12
[58] Field of Search .................... 128/3, 12, 13, 14, 15, 128/16, 17, 18, 20

[56] References Cited

U.S. PATENT DOCUMENTS

| | | | |
|---|---|---|---|
| 252,127 | 1/1882 | Morrill | 128/15 |
| 1,193,782 | 8/1916 | Henderson | 128/15 |
| 1,319,904 | 10/1919 | Roberts | 128/12 |
| 2,690,745 | 10/1954 | Govan | 128/15 |
| 2,756,742 | 7/1956 | Barton | 128/15 |
| 4,024,859 | 5/1977 | Slepyan et al. | 128/12 |
| 4,064,873 | 12/1977 | Swenson | 128/12 |

OTHER PUBLICATIONS

V. Mueller & Co., Chicago-1938 Catalog-p. 120.
Amico-Fine Surgical Instruments, ©1966 Catalog, pp. 352-353.

Primary Examiner—Robert W. Michell
Assistant Examiner—Arthur S. Rose
Attorney, Agent, or Firm—Phillips, Moore, Weissenberger, Lempio & Majestic

[57] ABSTRACT

An improved tongue blade that may be used with frames of conventional design and forming part of a mouth gag, said blade having a handle portion that connects with a frame and a tongue-engaging portion that extends from said handle portion at an obtuse angle of between 100° and 120°, said blade providing an improved exposure of the tonsils for surgical removal. The improved exposure is uniquely attained in the lower pole for more complete removal of the tonsil, and easier access to bleeding vessels for quicker ligation of bleeders.

6 Claims, 8 Drawing Figures

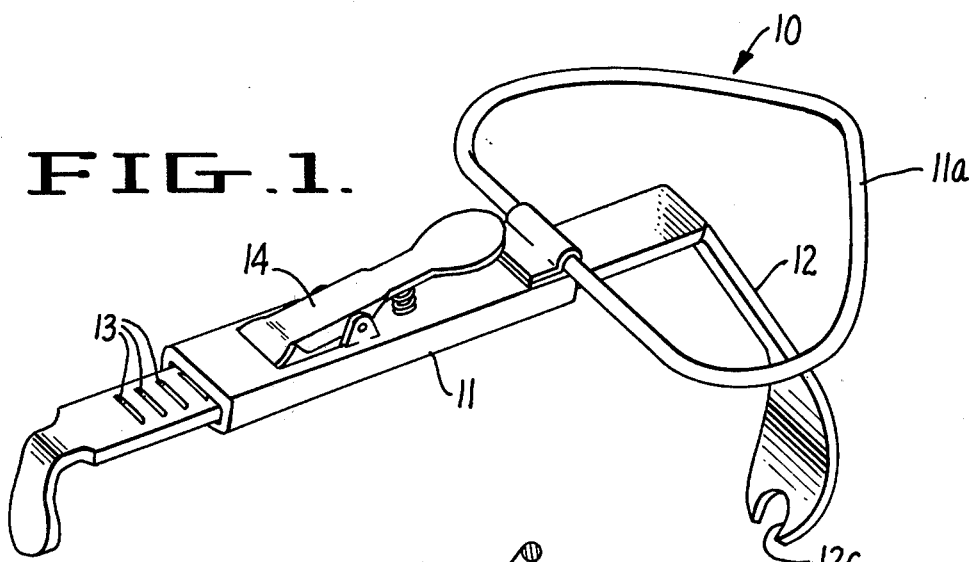
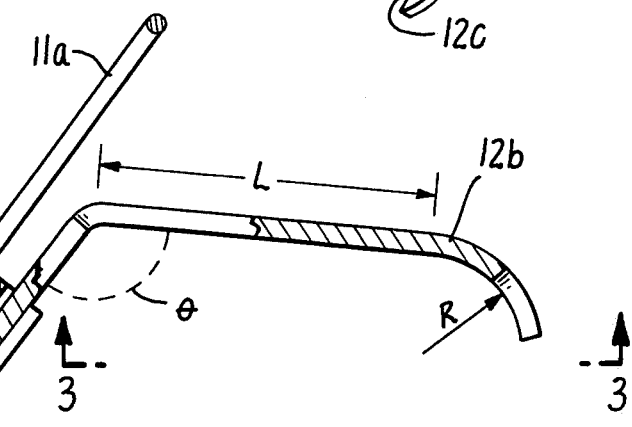
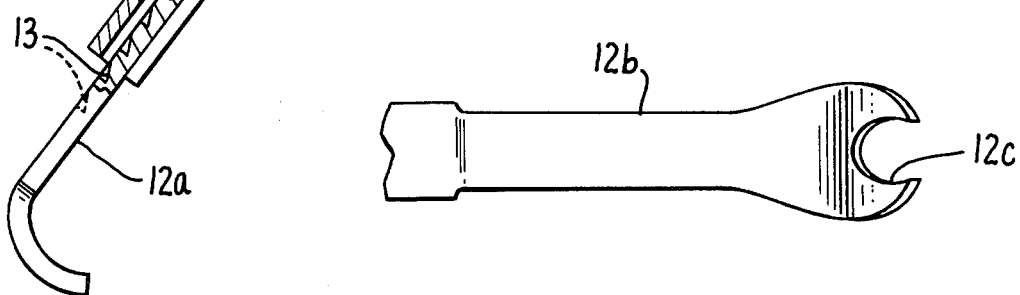

TONGUE BLADE FOR MOUTH GAG FOR ADULTS

BACKGROUND OF THE INVENTION

This invention relates generally to mouth gags and more particularly to an improved tongue blade for use with frames or holders of conventional design. As compared with tongue blades of the existing art, the improved tongue blade of this invention permits much wider opening of the mouth at the level of the incisor teeth while simultaneously applying less pressure at the level of the tonsillar pillars and soft palate, and this is accomplished without unduly stretching the temporomandibular joint. As a consequence, the relaxed soft palate is more easily retracted to allow better vision of the naso-pharynx, as well as easier access to the adenoids for purposes of surgical removal. Relaxed tonsillar pillars also facilitate the dissection of the tonsils and provide a better view of the lower pole. In addition, better exposure and access facilitates the ligation of bleeders.

Prior art tongue blades essentially consist of a curved tongue-engaging portion that connects to a handle at approximately a right angle; and in some instances the tongue-engaging portion actually connects at an acute angle. The tongue blades of the present invention, however, are formed with tongue-engaging portions comprising an essentially straight section that projects from the handle at an obtuse angle which may vary between 100° and 120°. The obtuse angular connection coacts synergistically with a curved tip formed on a radius of curvature less than one and one-half inches to provide a localized pressure directly in front of the lingual tonsil. The resultant effect is materially different from the pressure contact and performance afforded by prior art tongue blades which stretch the temporomandibular joint by applying pressure largely in the region of the tonsillar pillars and soft palate. Adults are more prone to damage of the temporomandibular joint from excessive stretching than children; in some adults, arthritis occasionally results. Since only a few tonsillectomies have been done on adults with an obtuse angle tongue blade according to the present invention, as compared with the number performed on children, it is not yet known if there is an optimum angle between 100° and 120°. So far, using an obtuse angle of 110° or 115° in a tongue blade has provided the desired increased opening of the mouth.

Reference is suggested to related patent, U.S. Pat. No. 4,064,873, issued to the inventor of the present invention, wherein an obtuse tongue blade found to be more favorably used with children is disclosed.

Thus, a principal object of the present invention is to provide an improved tongue blade primarily for adults that is adapted for use with most conventional frames for a mouth gag.

BRIEF DESCRIPTION OF THE DRAWINGS

In the drawings, forming a part of this application, and in which like parts are identified by like reference numerals throughout the same, FIG. 1 is a perspective view of a mouth gag comprising a conventional frame and a tongue blade formed in accordance with the present invention;

FIG. 2 is a side view of the mouth gag, a portion of the tongue blade being shown in center section;

FIG. 3 is a bottom plan view of a portion of the tongue blade as viewed on the lines 3—3 of FIG. 2;

DESCRIPTION OF A PREFERRED EMBODIMENT

Figure 4:
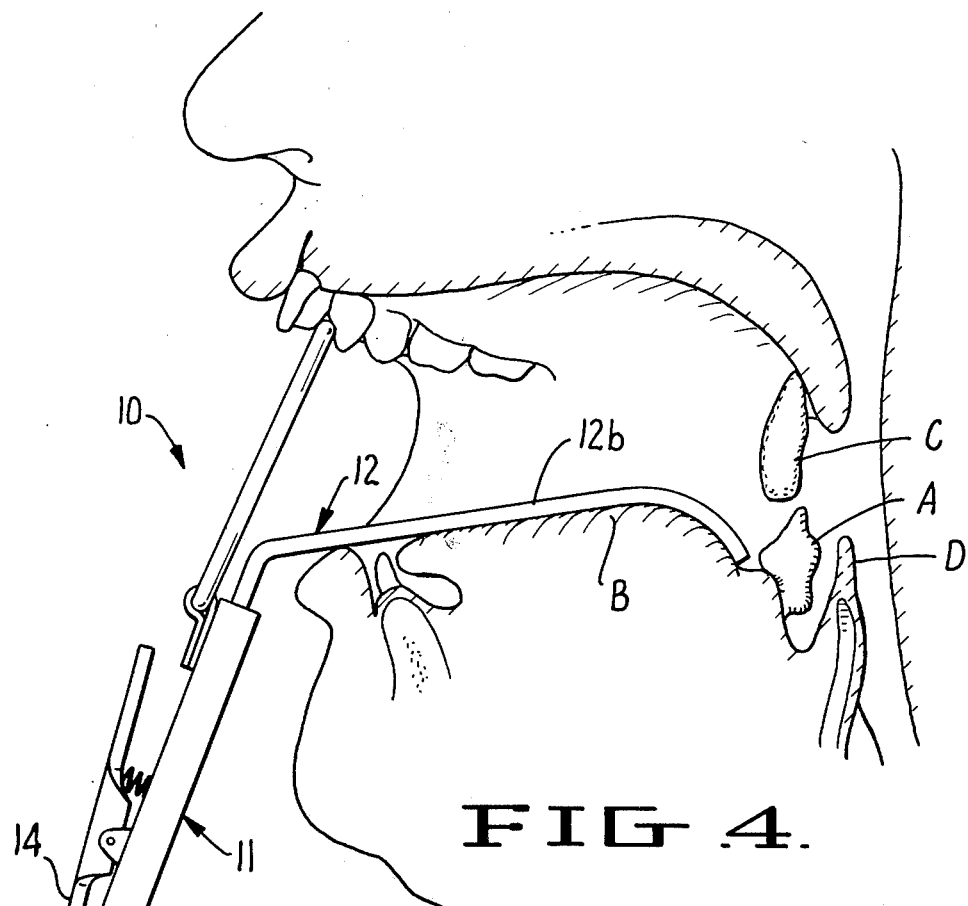
FIG. 4 is a side elevation of the mouth gag inserted in the mouth of a patient, and showing the position of the tongue blade and pressure contact.

Referring to FIG. 1, there is illustrated a mouth gag 10 comprising a frame 11, including a forward projecting rod 11a that engages the upper teeth, and a tongue blade 12. Frame 11 is conventional in construction and is commonly known as a McIvor frame. Tongue blade 12, however, as in FIGS. 2 and 3, is made in accordance with the teaching of this invention and comprises a substantially straight handle 12a and a tongue-engaging portion 12b consisting of an essentially straight elongated section connected at a first end to said handle portion and having an opposite distal end, said distal end including a curved tip which has a semicircular opening 12c to guide the endotracheal tube for anesthesia. A rack-like surface is formed on the back side of handle 12a by a plurality of grooves 13 which are engaged by a pawl 14 pivotally connected to frame 11. This structural detail is conventional to the McIvor frame and serves merely to adjustably position the tongue blade relative to the frame.

Figure 5:
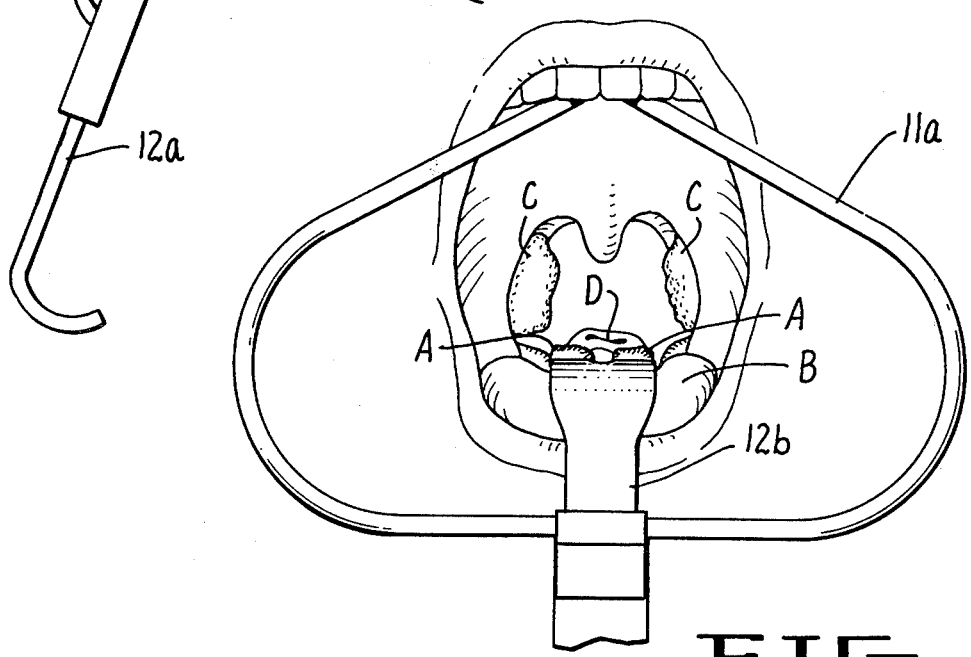
FIG. 5 is a front view looking into the mouth of the patient with the mouth gag in place.

The present invention is more particularly directed to the angular extension, shape and length of tongue-engaging portion 12b. Referring to FIG. 2 in particular, it will be noted that tongue-engaging portion 12b extends from the handle 12a at an obtuse angle $\theta$. In addition, the tongue-engaging portion possesses a curved tip formed with a radius of curvature R at a distance L from handle portion 12a. The relationship of angle $\theta$, the distance L and the curvature R are selected (depending on the mouth size and mouth configuration of the patient) to apply a pressure contact directly in front of the lingual tonsil A, as shown in FIGS. 4 and 5. It has been empirically determined that for adults, angle $\theta$ may vary between 100° and 120°; the dimension L must be at least two inches in length; and the radius of curvature R must be less than one and one-half inches.

Figure 6:
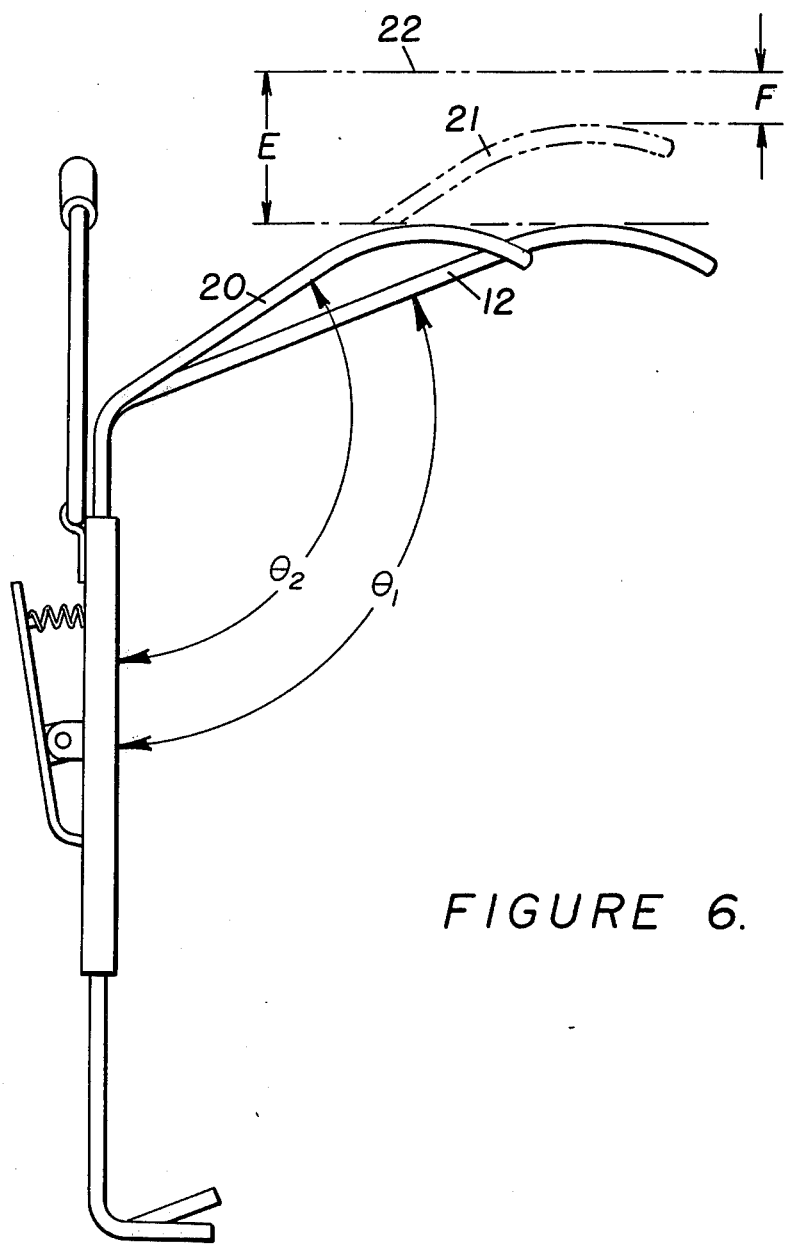
FIG. 6 illustrates an obtuse angle tongue blade for children in comparison with an obtuse angle tongue blade according to the present invention.

FIG. 6 illustrates a comparison between an obtuse angle tongue blade 12 according to the present invention with a tongue blade 20 according to U.S. Pat. No. 4,064,873, wherein the obtuse angle is disclosed and claimed as being in the range between 120° and 135°. In research performed subsequent to the filing of U.S. Pat. No. 4,064,873, the inventor found that a tongue blade having an obtuse angle $\theta$ of 110° and 115° provided the best results for larger adult males. This empirical result was not initially discovered since the obtuse angle tongue blade was originally tested mostly on children, those on whom tonsillectomies are most often performed.

As seen in FIG. 6, as the tongue-engaging part of the tongue blade is made longer, as at 12, a less obtuse angle $\theta$ is needed to provide substantially the same improved mouth opening E, between the tongue blade and the roof of the mouth 22, thereby providing the same improved visibility of the tonsils as had been obtained with tongue blade 20. FIG. 6 illustrates, for example, that to obtain a degree of mouth opening with the longer tongue blade 12, equal to the opening enabled with a shorter child's tongue blade 20 having an angle $\theta_2$ of 122°, a $\theta_1$ of approximately 110° would be needed. Shown in phantom at 21 is the longer tongue blade if the same angle $\theta$ of 122° were used. As can be seen, this provides a smaller opening F in the mouth than would otherwise be available, and would therefore be so inadequate as to make surgery impossible.

As indicated above, the exact configuration and dimensions of the blade may vary from patient to patient. Accordingly, a series of tongue blades should be provided for use in combination with a single frame. Because of size differences, the overall length of the tongue-engaging portion of the blade may vary between two inches and five inches while the dimension L varies between one and one-half inches and four inches in length. The curved tip of the blade may also vary depending on size. It has been empirically determined that best results will be obtained if the tip is between three-fourths inch and one and one-half inches in length.

In operation, as seen in FIGS. 4 and 5, when the curved tip of tongue blade 12 is placed directly in front of lingual tonsils A, a slight pressure on the tongue B will cause the lingual tonsils to protrude upward bringing the lingual tonsils into excellent view while fully exposing the faucial tonsils C and epiglottis D. Thus, even the rarely required lingual tonsillectomy can be accomplished with excellent access and direct vision.

Figure 7B:
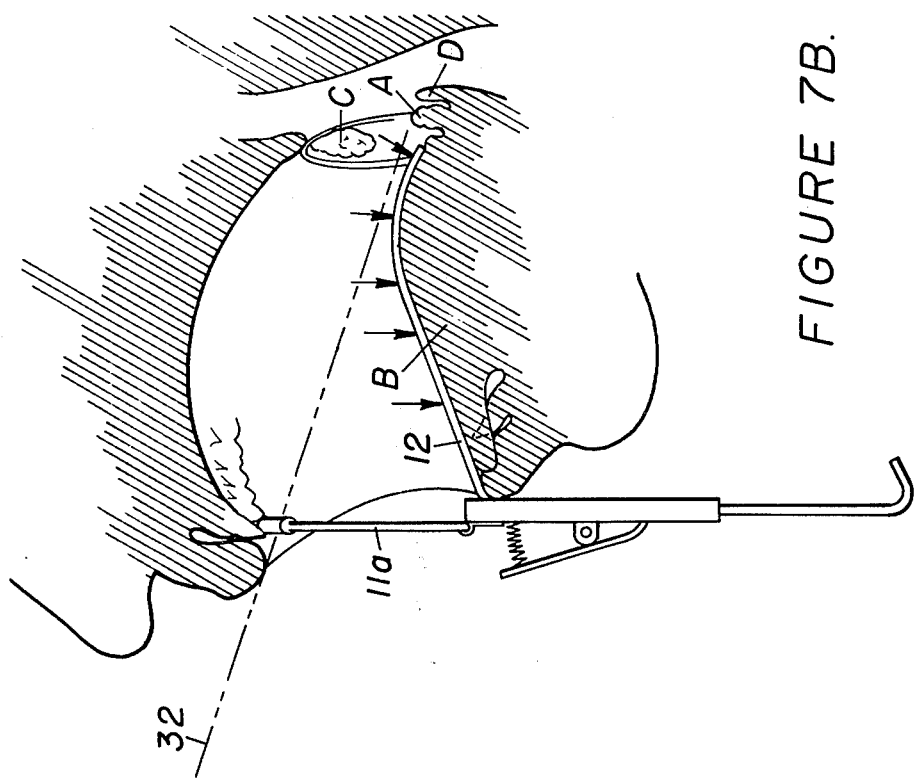
FIG. 7B illustrates the operation of a mouth gag according to the present invention including an obtuse angle tongue blade.
Figure 7A:
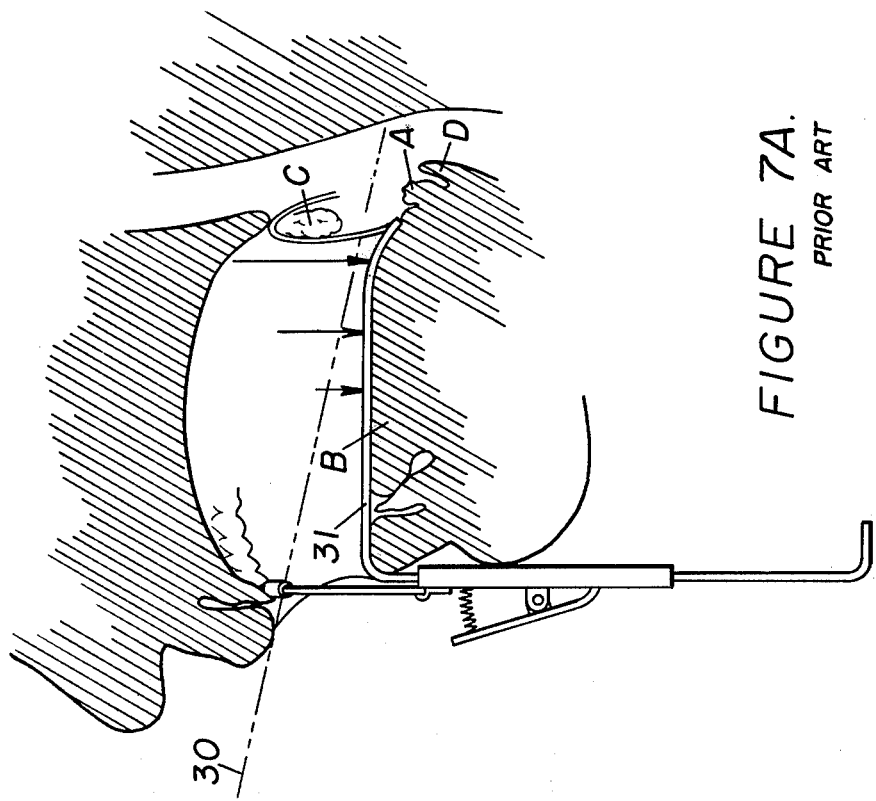
FIG. 7A illustrates the operation of a prior art mouth gag with a right angle tongue blade.

FIGS. 7A and 7B illustrate how the operation of a mouth gag according to the present invention, including an obtuse angle tongue blade 12, allows for much greater opening of the mouth, in an amount up to twice as wide as a mouth gag including a right angle blade 31. This provides improved visibility and access, while avoiding excessive stretching of the temporomandibular joint. The dotted line 30 of FIG. 7A shows the line of sight available to a surgeon using a prior art tongue blade, while dotted line 32 of FIG. 7B shows the improved visibility obtained with an obtuse angle tongue blade, showing that in many cases the lingual tonsils A and epiglottis D will now be directly visible.

Also illustrated in FIGS. 7A and 7B are arrows which show in a general way the improved lesser pressure on the tongue B of FIG. 7B from tongue blade 12 as compared with the pressure exerted on tongue B in FIG. 7A due to the operation of tongue blade 31. As can be seen, the pressure applied on certain areas of the tongue in FIG. 7A is considerably greater and is directed substantially in a downward direction mainly on the back half of the tongue. On the other hand, the pressure exerted on the tongue in FIG. 7B is much less and more even, and is directed such that the tongue is drawn slightly forward, further enhancing exposure of the throat. Note that in practice, if the tongue is displaced forward far enough by the operation of the apparatus of the present invention such that it would rest between the tongue blade and incisor teeth, the tip of the tongue is merely pushed to one side.

Although a preferred embodiment of the invention has been illustrated and described, various types of frame holders may be used as well as other modifications and changes without departing from the spirit of the invention or the scope of the appended claims, and each of such modifications or changes is contemplated.

What is claimed is:

1. A series of tongue blades in combination with a frame, said tongue blades being formed in various sizes, each blade having a substantially straight handle portion adapted to be connected to said frame in order to form a mouth gag and a substantially straight elongated tongue-engaging portion connected at a first end to said handle portion and having an opposite distal end, said tongue engaging portion extending from said handle portion at an obtuse angle between 100° and 120°, said tongue-engaging portion having a curved tip that is formed with a radius of curvature less than one and one-half inches a distance greater than two inches from said handle portion whereby the handle portion and tongue-engaging portion of each tongue blade defines an unobstructed obtuse angular void therebetween extending from the handle portion a distance of at least two inches and a semi-circular opening at the distal end of said curved tip for guiding an endotracheal tube for anesthesia.

2. A mouth gag having a frame, a blade having a substantially straight handle portion that is connected to said frame and a substantially straight elongated tongue-engaging portion connected at a first end to said handle portion and having an opposite distal end, said tongue-engaging portion extending from said handle portion at an obtuse angle of between 100° and 120°, said tongue-engaging portion having at said distal end a curved tip with a semi-circular opening for guiding an endotracheal tube for anesthesia, said tongue—engaging portion being at least one and one-half inches in length, said curved tip having a radius of curvature less than one and one-half inches, said handle portion and tongue-engaging portion defining an unobstructed obtuse angular void therebetween that extends from the handle portion a distance of at least two inches.

3. The tongue blade of claim 2, said tongue-engaging portion of said blade having an overall length of between two inches and five inches.

4. The tongue blade of claim 2, the tongue-engaging portion of said blade being less than four inches in length.

5. The tongue blade of claim 2, the curved tip of said blade being between three-fourths inch and one and one-half inches in length.

6. The tongue blade of claim 2, the curved tip of said blade having a radius of curvature equal to or greater than one-half inches in length.

* * * * *